(12) United States Patent
Ho

(10) Patent No.: US 11,883,548 B2
(45) Date of Patent: Jan. 30, 2024

(54) DISPLAY DEVICE WITH ULTRAVIOLET GERMICIDAL LAMP

(71) Applicant: OXTI CORPORATION, New Taipei (TW)

(72) Inventor: Chih-Feng Ho, New Taipei (TW)

(73) Assignee: OXTI CORPORATION, New Taipei (TW)

(*) Notice: Subject to any disclaimer, the term of this patent is extended or adjusted under 35 U.S.C. 154(b) by 422 days.

(21) Appl. No.: 17/337,425

(22) Filed: Jun. 3, 2021

(65) Prior Publication Data

US 2022/0105209 A1 Apr. 7, 2022

(30) Foreign Application Priority Data

Oct. 5, 2020 (TW) ................................. 109213024

(51) Int. Cl.
*A61L 2/10* (2006.01)
*H05B 47/115* (2020.01)
*H05B 47/19* (2020.01)

(52) U.S. Cl.
CPC .............. *A61L 2/10* (2013.01); *H05B 47/115* (2020.01); *H05B 47/19* (2020.01); *A61L 2202/11* (2013.01); *A61L 2202/14* (2013.01)

(58) Field of Classification Search
CPC .... A61L 2/10; A61L 2202/11; A61L 2202/14; A61L 2/26; H05B 47/115; H05B 47/19; Y02B 20/40
USPC ........................... 250/454.11, 455.11, 504 R
See application file for complete search history.

(56) References Cited

U.S. PATENT DOCUMENTS

2021/0369885 A1* 12/2021 Lee ........................... A61L 2/26
2022/0134128 A1* 5/2022 Kuzelka ............... A61N 5/0624
422/24

* cited by examiner

*Primary Examiner* — Michael Maskell
(74) *Attorney, Agent, or Firm* — Leong C. Lei

(57) ABSTRACT

The display device with an ultraviolet (UV) germicidal lamp includes a display device, an UV germicidal lamp, a power electrically connected to the UV germicidal lamp, a control circuit electrically connected to the UV germicidal lamp, and a fixture member detachably fixing the UV germicidal lamp to a circumferential rim of the display device. The fixture member includes a base, a first clamp piece, and a second clamp piece. The base is joined to the UV germicidal lamp. The first and second clamp pieces are mounted at interval on the base, forming a clamp interval in between. An elastic element is provided between the second clamp piece and the base for forcing the second clamp piece towards the first clamp piece. Therefore, by adjusting the clamp interval, the UV germicidal lamp may be reliably clamped to the display device.

6 Claims, 8 Drawing Sheets

DISPLAY DEVICE WITH ULTRAVIOLET GERMICIDAL LAMP

BACKGROUND OF THE INVENTION

(a) Technical Field of the Invention

The present invention is generally related to display devices, and more particular to a display device with an ultraviolet germicidal lamp fixed to its rim.

(b) Description of the Prior Art

A display device is the most important output device for a computer, regardless of whether the computer is for industrial, commercial, or home application.

Republic of China, Taiwan, Patent No. M387206 teaches a lamp for a display device, and the lamp includes a light member, a positioning member, and a rack member. The positioning member fixes the light member to the display device. The light member may be a traditional light source or a light source using LED or OLED. The positioning member includes a base, clamp pieces, gears, and a lever. The level engages the gears, which in turn drives the clamp pieces, so that the positioning member is reliably clamped to a rim of the display device.

The positioning member of the lamp is rather complicated. On the other hand, the global outbreak of pandemics such as SARS in the past and COVID-19 recently prompts people to realize that display devices, especially when they are used by different persons, could be a hotbed for germs and viruses. There is a need for the light member of the above-described lamps on display devices to provide sterilization.

SUMMARY OF THE INVENTION

To achieve the above objectives, the present invention provides a display device with an ultraviolet (UV) germicidal lamp, which includes a display device having a circumferential rim, an UV germicidal lamp, a power electrically connected to the UV germicidal lamp, a control circuit electrically connected to the UV germicidal lamp, and a fixture member detachably fixing the UV germicidal lamp to the circumferential rim of the display device. The fixture member includes a base, a first clamp piece, and a second clamp piece. The base is joined to the UV germicidal lamp. The first clamp piece and the second clamp piece are mounted at interval on the base, thereby forming a clamp interval in between. An elastic element is provided between the second clamp piece and the base for forcing the second clamp piece slidably towards the first clamp piece.

Preferably, the first clamp piece is immediately stacked on the second clamp piece.

Preferably, two troughs are provided respectively and oppositely along two opposing lateral inner walls of the base, and wo lateral edges of the first clamp piece and two lateral edges of the second clamp piece are respectively and slidably embedded in the troughs.

Preferably, a connector is provided along a side of the base.

Preferably, the display device with UV germicidal lamp further includes a signal receiver electrically connected to the control circuit for receiving a wireless signal from a mobile device.

Preferably, a sensor is electrically connected to the control circuit for detecting the proximity of a human body.

As described above, by sliding the first clamp piece relative to the second clamp piece to adjust the clamp interval, the UV germicidal lamp may be reliably clamped to the circumferential rim of the display device.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
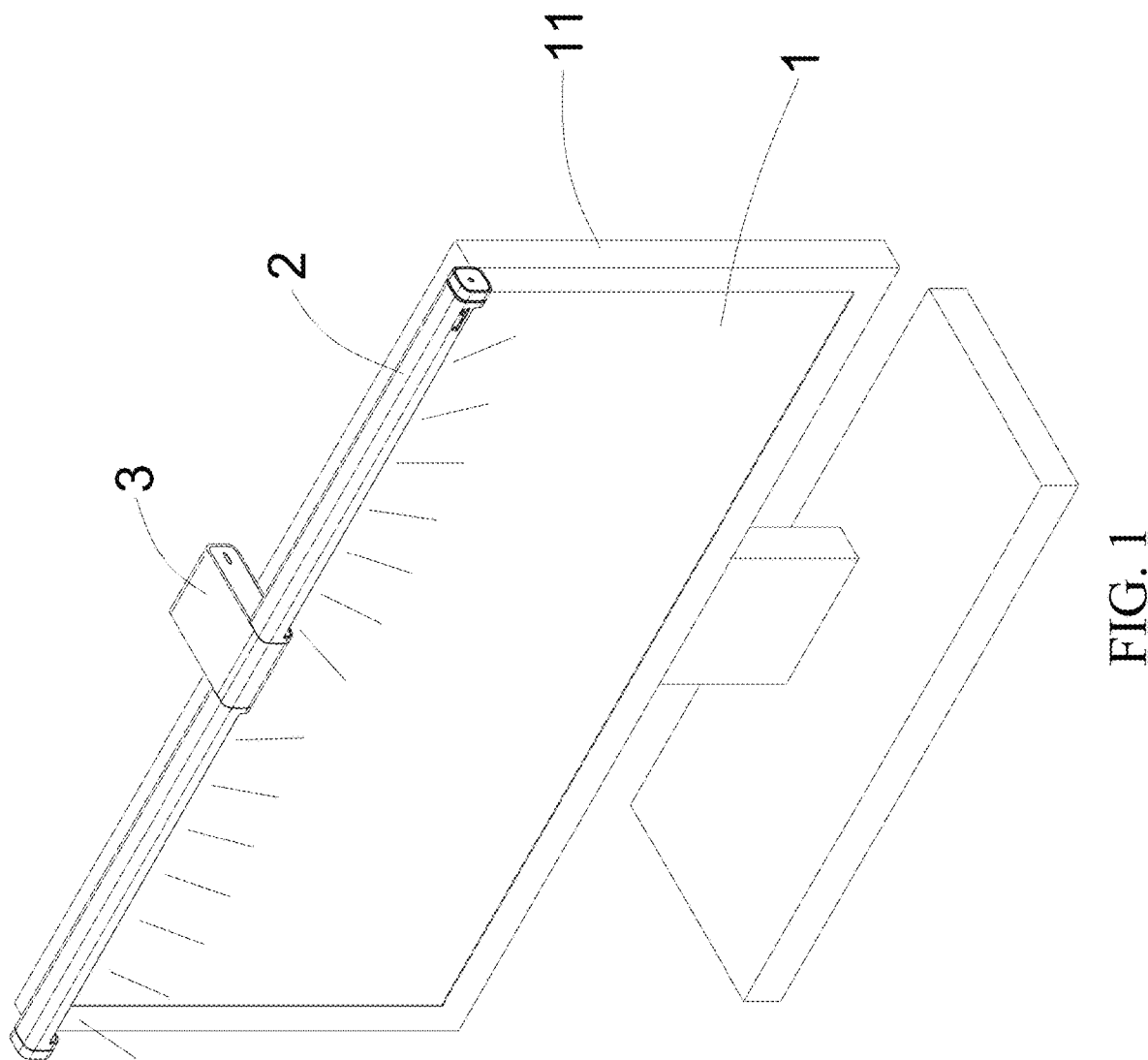
FIG. 1 is a perspective diagram showing a display device with an ultraviolet (UV) germicidal lamp according to an embodiment of the present invention.
Figure 2:
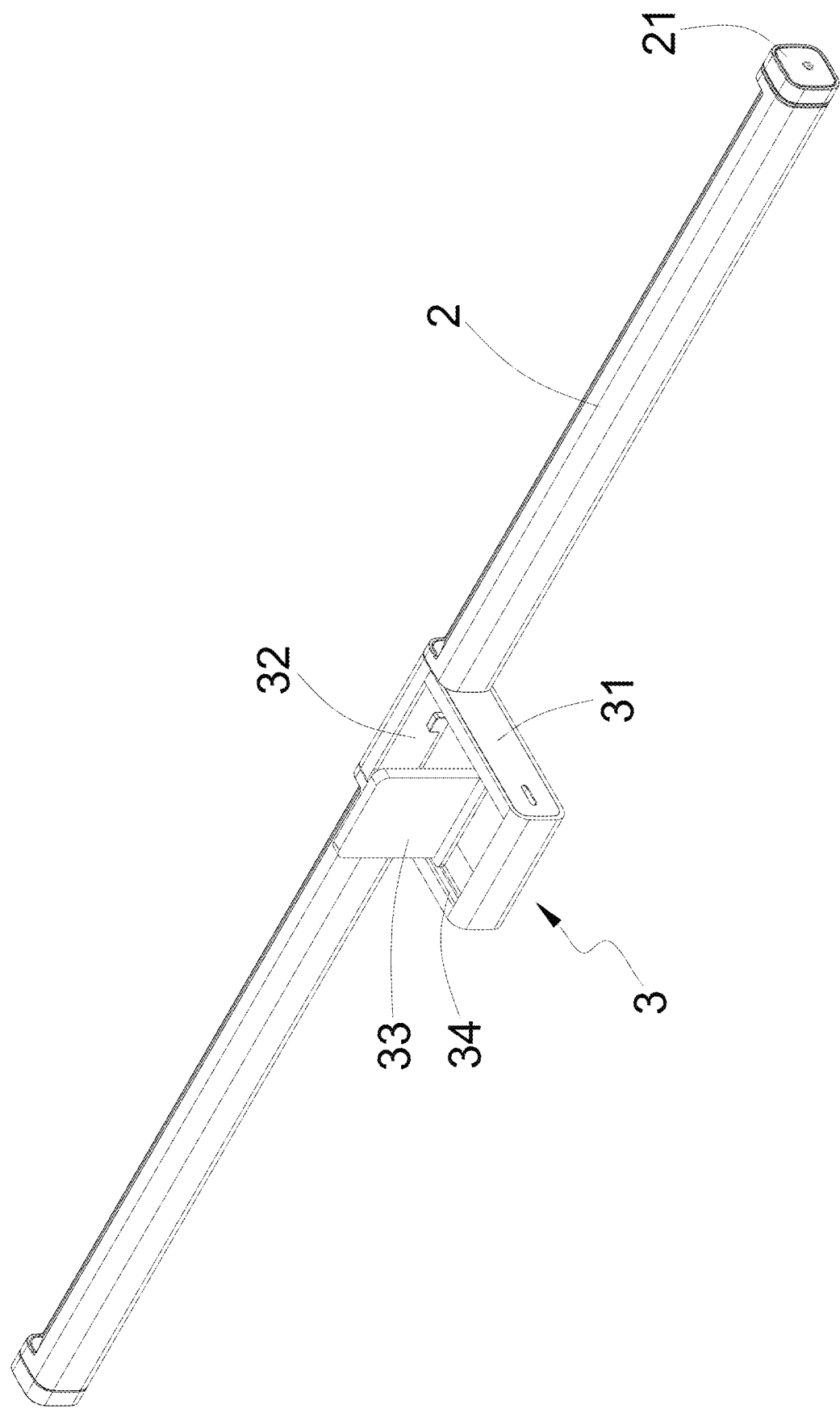
FIG. 2 is a perspective diagram showing the UV germicidal lamp of FIG. 1.
Figure 6:
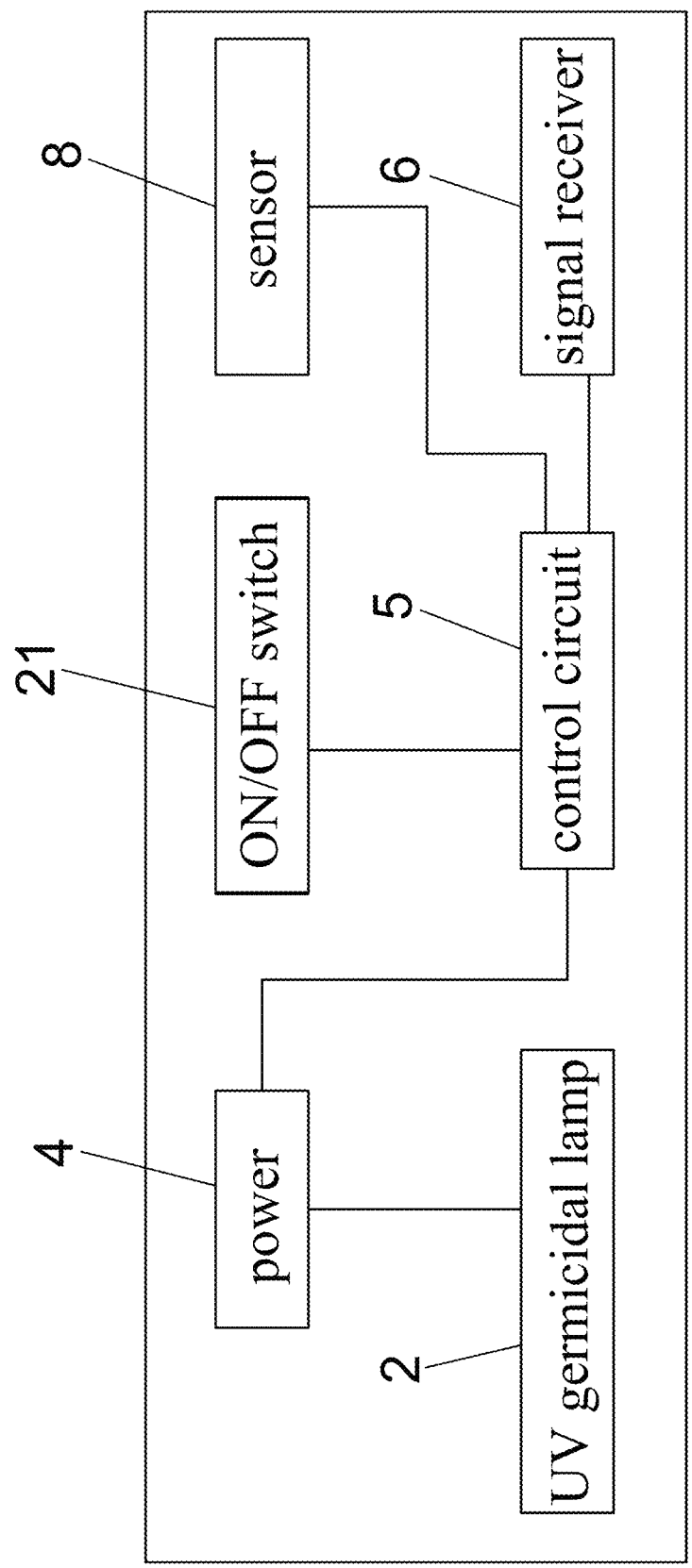
FIG. 6 is a functional block diagram showing a display device with an UV germicidal lamp according to the present invention.

As shown in FIGS. 1 and 2, as well as FIG. 6, a display device with an ultraviolet (UV) germicidal lamp according to an embodiment of the present invention includes a display device 1, an UV germicidal lamp 2, a power 4, a control circuit 5, and a fixture member 3.

The display device 1 may be a Liquid Crystal Display (LCD), an Organic Light-Emitting Diode (OLED) display, or other similar display device. The display device 1 has a circumferential rim 11.

The UV germicidal lamp 2 is mounted on the circumferential rim 11 of the display device 1. The UV germicidal lamp 2 is configured with a ON/OFF switch 21 to an end.

The ON/OFF switch 21 is for turning on or off the UV germicidal lamp 2. A first press of the ON/OFF switch 21 turns on the UV germicidal lamp 2 and the UV germicidal lamp 2 produces an ultra-violet (UV) light. After the UV germicidal lamp 2 is turned on and the UV light has performed sterilization for a period of time, the UV germicidal lamp 2 would be automatically turned off. Alternatively, while the UV germicidal lamp 2 is turned on, pressing the ON/OFF switch 21 may also turn off the UV germicidal lamp 2 to stop the illumination by the UV light. The UV germicidal lamp 2 may be configured with an indicator member to inform whether the sterilization is completed. The indicator member may be an indicator lamp, a buzzer, or an indicator display. The UV germicidal lamp 2 may be an UV lamp, a metal halide lamp, a high intensity discharge (HID) lamp, a mercury vapor lamp, or a fluorescent lamp. The UV lamp may be an UVA, UVB, or UVC lamp. An UV light has a bandwidth between 10 nm and 400 nm. UVA has a bandwidth between 320 and 400 nm, UVB is between 280 and 320 nm, and UVC between 100 and 280 nm. An ordinary UV light has a bandwidth between 200 nm and 280 nm.

The power 4 may be an external power source. The power 4 is electrically connected to the UV germicidal lamp 2. The control circuit 5 is configured within the fixture member 3. The control circuit 5 is electrically connected to the UV germicidal lamp 2 for turning on and off the UV germicidal lamp 2, the intensity of the UV germicidal lamp 2, and the duration of lighting.

Figure 3:
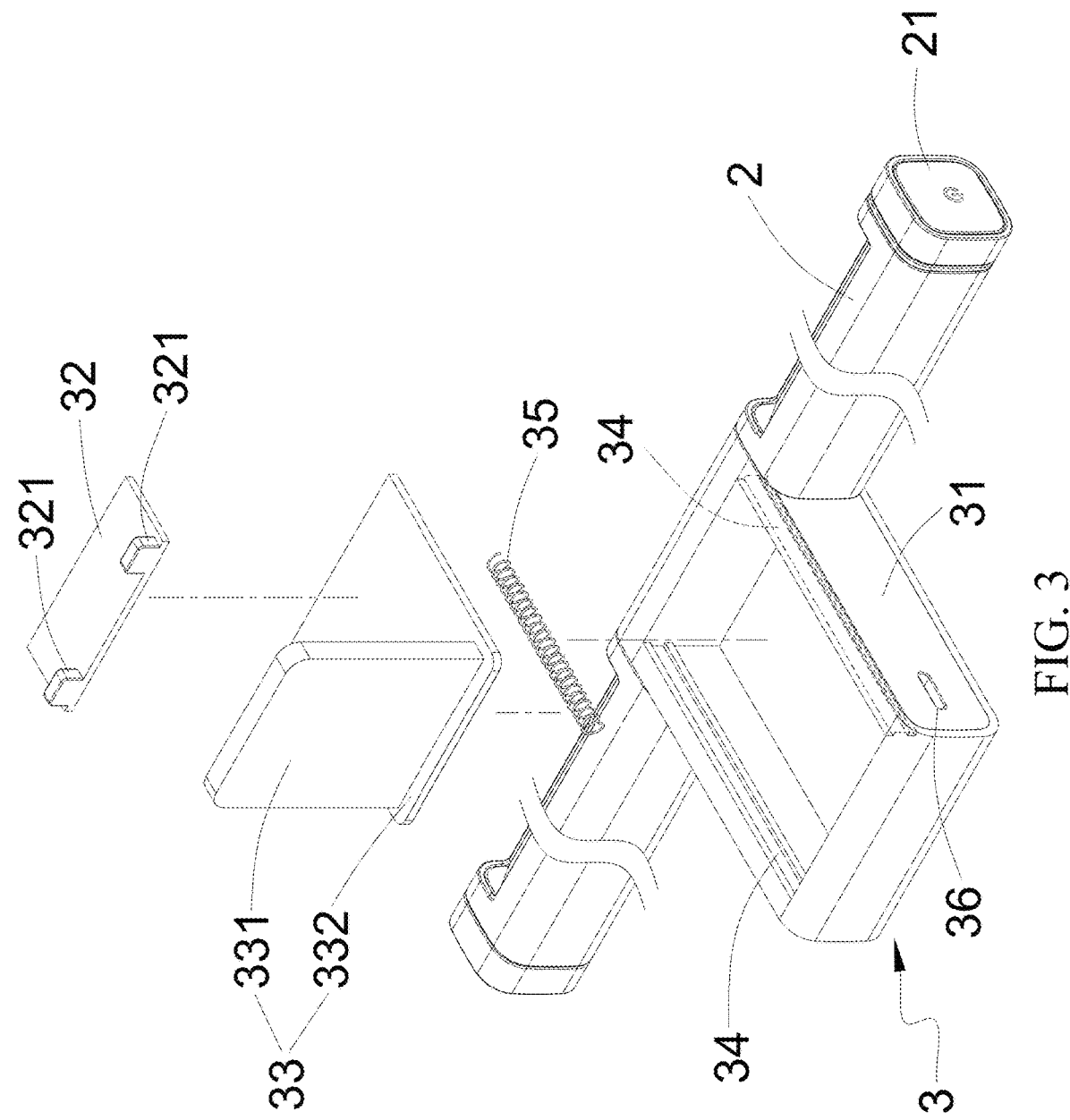
FIG. 3 is a perspective break-down diagram showing the UV germicidal lamp of FIG. 2.
Figure 4:
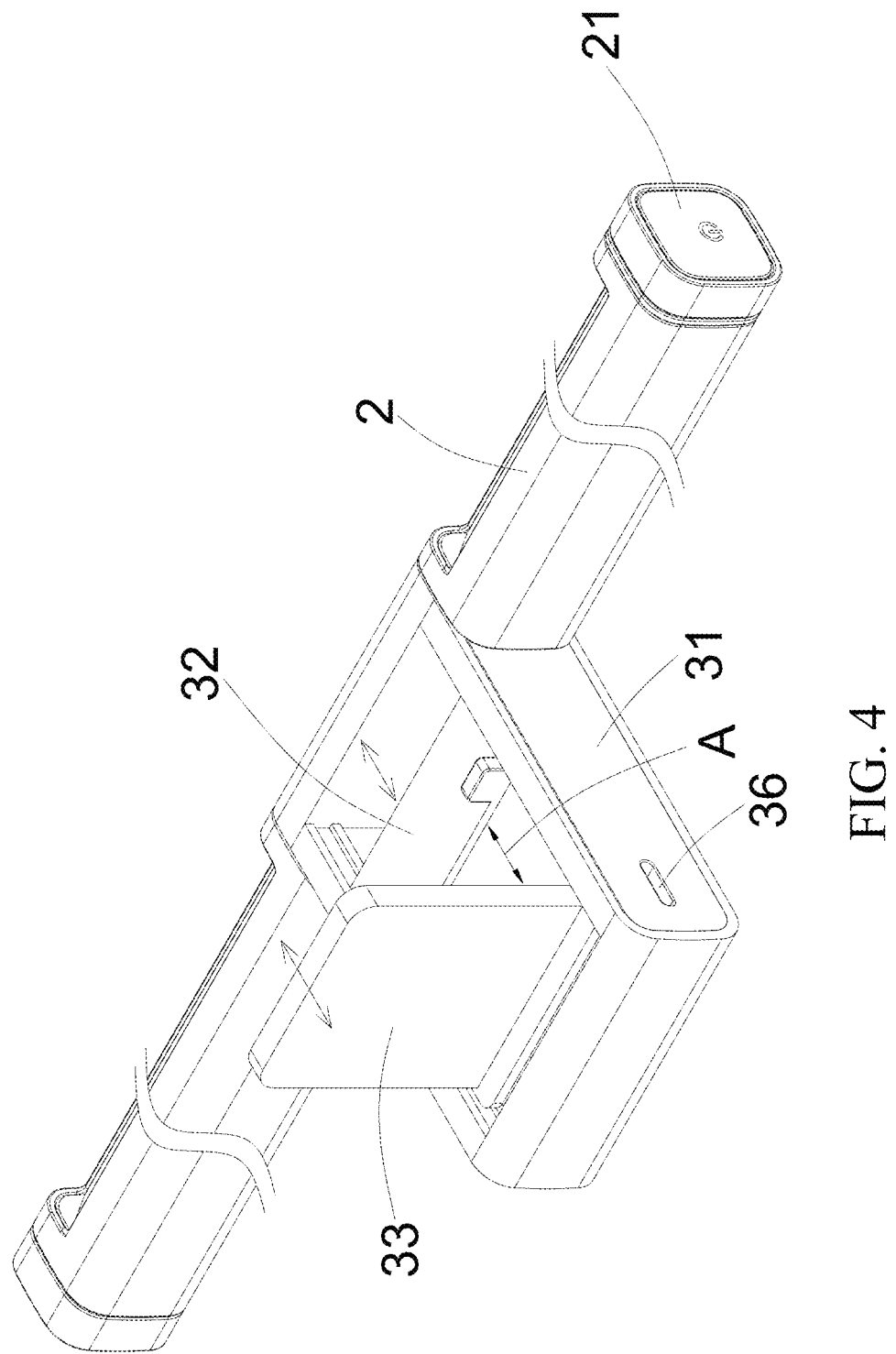
FIG. 4 is a perspective diagram depicting operation of a fixture member of the UV germicidal lamp of FIG. 2.

As shown in FIG. 3, the fixture member 3 fixes the UV germicidal lamp 2 to the circumferential rim 11 of the display device 1. The fixture member 3 includes a base 31, a first clamp piece 32, and a second clamp piece 33. The base 31 is joined to the UV germicidal lamp 2. The first clamp piece 32 and the second clamp piece 33 oppose each other, thereby forming a clamp interval A in between as shown in FIG. 4. An elastic element 35 is provided between the second clamp piece 33 and the base 31 so as to force the second clamp piece 33 towards the first clamp piece 32. The elastic element 35 may be a spring. A connector 36 is provided along a side of the base 31. The connector 36 is for connecting an external power 4 for powering the UV germicidal lamp 2, and it may be a Type-A or Type-C Universal Serial Bus (USB) connector.

More specifically, two troughs 34 are provided respectively and oppositely along two opposing lateral inner walls of the base 31. Two lateral edges of the first clamp piece 32, and those of the second clamp piece 33, are respectively embedded in the troughs 34. The first clamp piece 32 is stacked immediately on the second clamp piece 33. The first clamp piece 32 and the second clamp piece 33 may be L-shaped, where the first clamp piece 32 includes at least a first vertical piece 321 and a first lateral piece (not numbered), and the second clamp piece 33 includes a second lateral piece 332 and at least a second vertical piece 331. The first and second vertical pieces 321 and 331 are extended upward from the first and second lateral pieces respectively.

Figure 5:
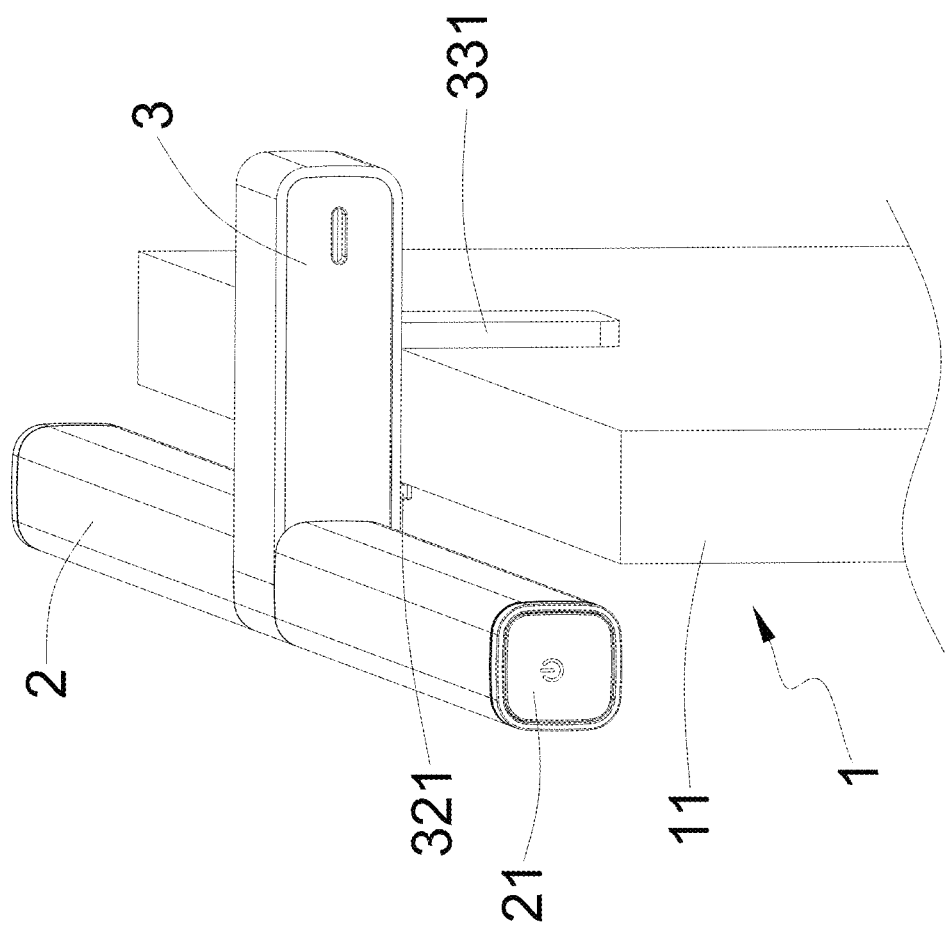
FIG. 5 is a perspective diagram depicting the fixation of the UV germicidal lamp on the display device.

As shown in FIGS. 3 and 4, by sliding the first clamp piece 32 and the second clamp piece 33, the clamp interval A may be adjusted. When the second clamp piece 33 is closer to the first clamp piece 32, the clamp interval A is reduced and, as shown in FIG. 5, the UV germicidal lamp 2 may be reliably clamped to the circumferential rim 11 of the display device 1. The adjustable clamp interval A allows the UV germicidal lamp 2 to fit on any display device 1 of various dimensions. On other hand, the UV germicidal lamp 2 provides sterilization to the display device 1 and the surrounding environment. The present invention provides a simplified structure, thereby achieving low production cost, convenient use, and low maintenance overhead.

Figure 7:
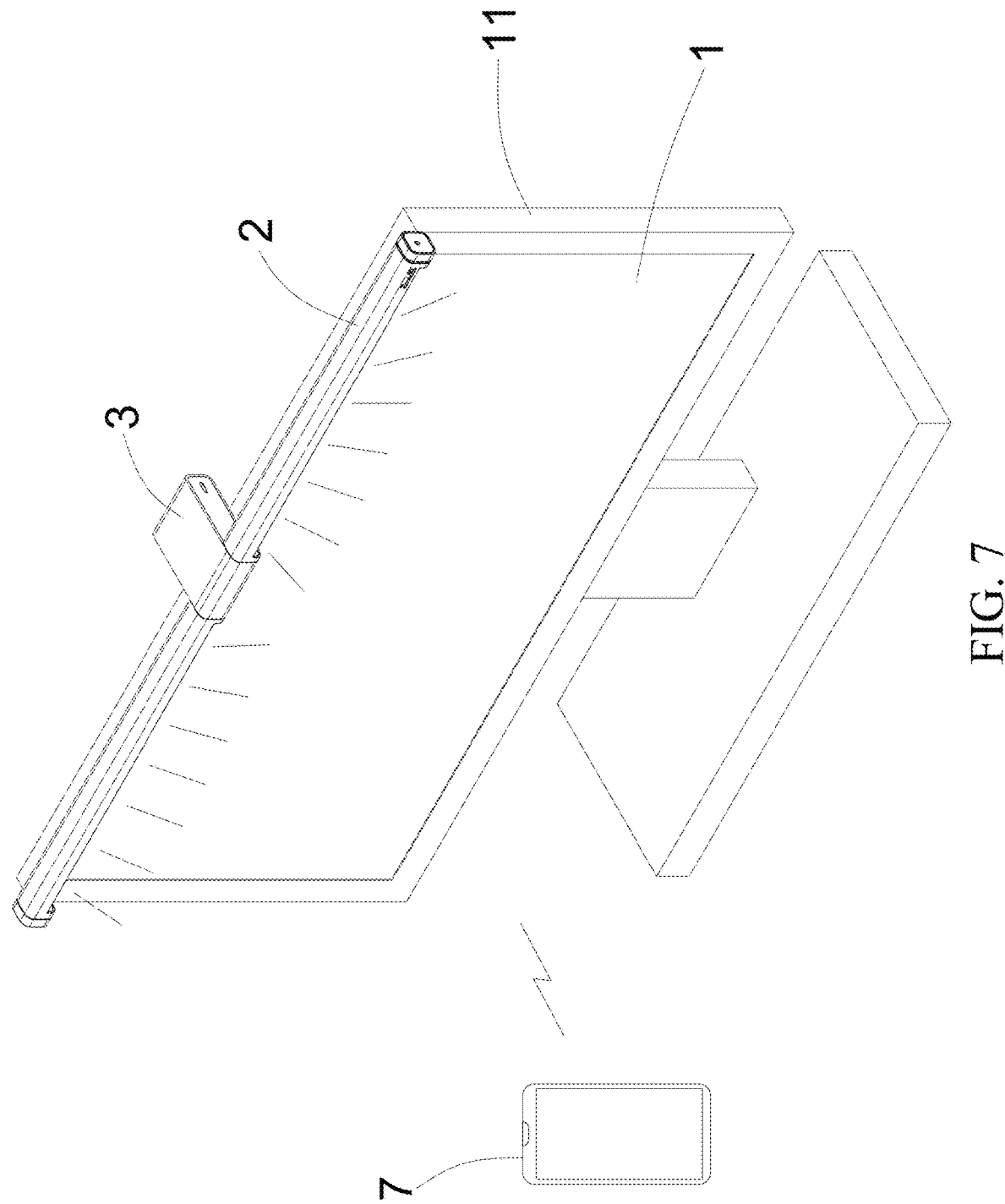
FIG. 7 is a perspective diagram showing a working scenario of the display device with an UV germicidal lamp of FIG. 1.

As shown in FIGS. 6 and 7, the control circuit 5 may be electrically connected to a signal receiver 6 configured within the fixture member 3. The signal receiver 6 receives a wireless signal from a remote controller or a mobile device 7. Based on the signal received by the signal receiver 6, the control circuit 5 selectively turns on or off the UV germicidal lamp 2, and adjusts the UV germicidal lamp 2's brightness and duration.

Figure 8:
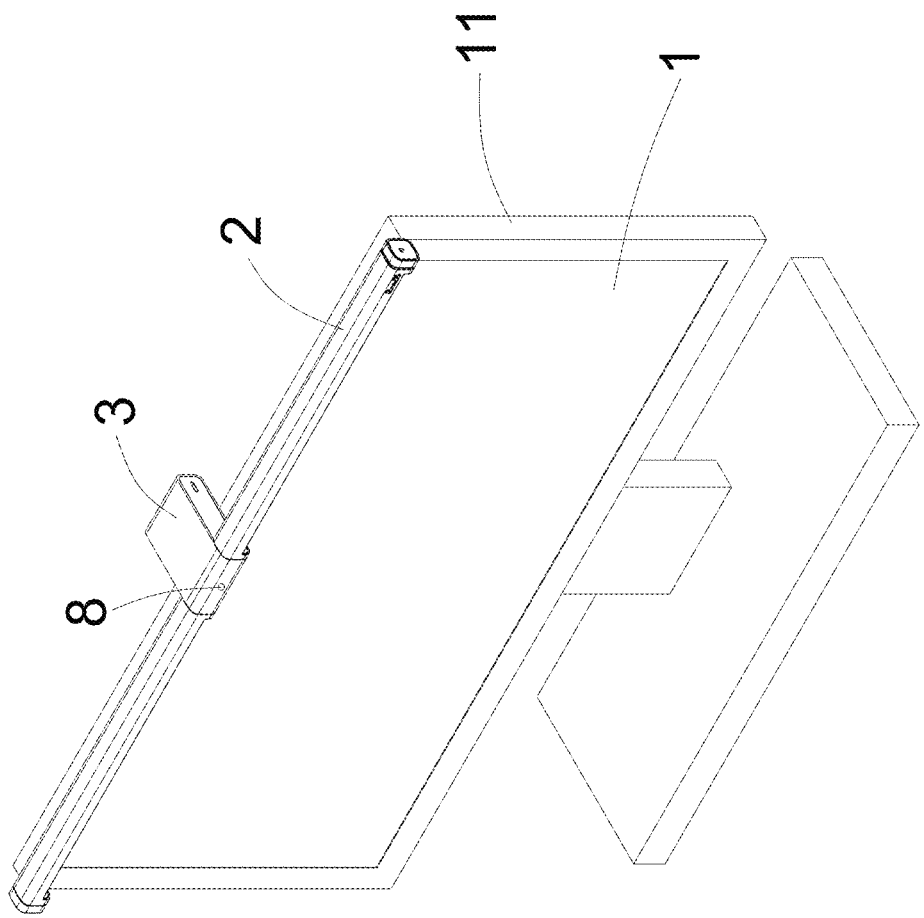
FIG. 8 is a perspective diagram showing another working scenario of the display device with an UV germicidal lamp of FIG. 1.
Figure 8:
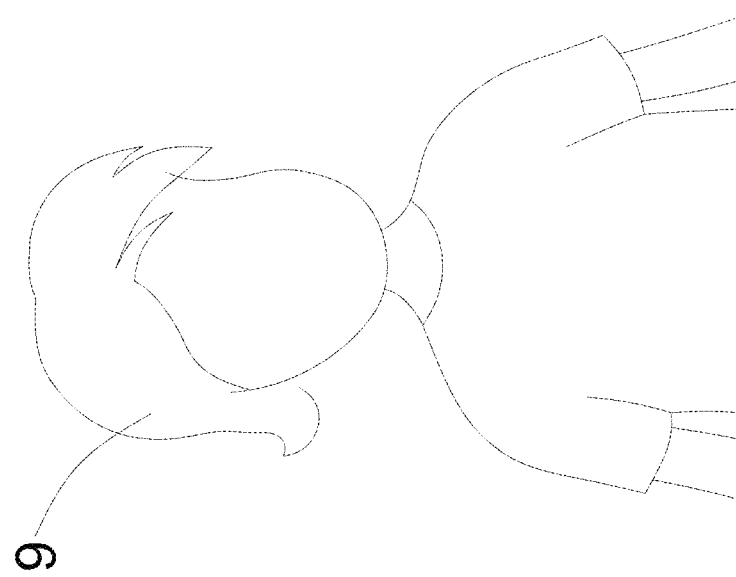

As shown in FIGS. 6 and 8, the control circuit 5 may be electrically connected to a sensor 8 for detecting the proximity of a human body 9. The sensor 8 may be configured on the fixture member 3 or along the circumferential rim 11 of the display device 1. The sensor 8 detects whether the human body 9 is present within a range around the display device 1. If the presence of the human body 9 is detected, the sensor 8 notifies the control circuit 5 and the control circuit 5 turns off the UV germicidal lamp 2 so not to cause mischief to the human body 9.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the claims of the present invention.

I claim:

1. A display device with ultraviolet (UV) germicidal lamp, comprising:
   a display device having a circumferential rim;
   an UV germicidal lamp;
   a power electrically connected to the UV germicidal lamp;
   a control circuit electrically connected to the UV germicidal lamp; and
   a fixture member detachably fixing the UV germicidal lamp to the circumferential rim of the display device;
   wherein the fixture member comprises a base, a first clamp piece, and a second clamp piece; the base is joined to the UV germicidal lamp; the first clamp piece and the second clamp piece are mounted at interval on the base, thereby forming a clamp interval in between; and an elastic element is provided between the second clamp piece and the base for forcing the second clamp piece slidably towards the first clamp piece.

2. The display device with UV germicidal lamp according to claim 1, wherein the first clamp piece is immediately stacked on the second clamp piece.

3. The display device with UV germicidal lamp according to claim 1, wherein two troughs are provided respectively and oppositely along two opposing lateral inner walls of the base; and wo lateral edges of the first clamp piece and two lateral edges of the second clamp piece are respectively embedded in the troughs.

4. The display device with UV germicidal lamp according to claim 1, wherein a connector is provided along a side of the base.

5. The display device with UV germicidal lamp according to claim 1, further comprising a signal receiver electrically connected to the control circuit for receiving a wireless signal from a mobile device.

6. The display device with UV germicidal lamp according to claim 1, further comprising a sensor electrically connected to the control circuit for detecting the proximity of a human body and notifying the control circuit to turn off the UV germicidal lamp.

* * * * *